(12) United States Patent
Haberkorn

(10) Patent No.: US 8,591,839 B2
(45) Date of Patent: Nov. 26, 2013

(54) SENSOR MODULE, TISSUE PROCESSOR, AND METHOD FOR OPERATING A TISSUE PROCESSOR

(75) Inventor: Claus Haberkorn, Dielheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 181 days.

(21) Appl. No.: 13/104,058

(22) Filed: May 10, 2011

(65) Prior Publication Data

US 2012/0003679 A1    Jan. 5, 2012

(30) Foreign Application Priority Data

Jun. 30, 2010   (DE) .......................... 10 2010 017 667

(51) Int. Cl.
*A61B 10/00*    (2006.01)
(52) U.S. Cl.
USPC ............. 422/563; 422/50; 422/501; 422/502; 436/180
(58) Field of Classification Search
USPC ...................... 422/536, 50, 501–502; 436/180
See application file for complete search history.

(56) References Cited

U.S. PATENT DOCUMENTS

| | | | |
|---|---|---|---|
| 3,789,662 A * | 2/1974 | Zettler et al. .................... | 374/31 |
| 2005/0233409 A1 | 10/2005 | Posthuma | |
| 2006/0148063 A1 | 7/2006 | Fauzzi et al. | |
| 2007/0243626 A1 | 10/2007 | Windeyer et al. | |
| 2010/0129859 A1 | 5/2010 | Allen et al. | |

FOREIGN PATENT DOCUMENTS

| | | |
|---|---|---|
| DE | 4117830 | 4/2004 |
| WO | 91/13335 A1 | 9/1991 |
| WO | 2004/029584 A1 | 4/2004 |

OTHER PUBLICATIONS

UK Intellectual Property Office, Office Action for GB Appl. No. 1104778.4 corresponding to U.S. Appl. No. 13/104,058, Jul. 25, 2011.
United Kingdom Intellectual Property Office, Examination Report under Section 18(3) mailed Jul. 31, 2012 in corresponding Application No. GB1104778.4.

* cited by examiner

*Primary Examiner* — Jyoti Nagpaul
(74) *Attorney, Agent, or Firm* — Hodgson Russ LLP

(57) ABSTRACT

A sensor module (38, 40, 42) for a tissue processor (20) has a thermal sensor (66) for measuring a temperature of a container (30, 32, 34) of the tissue processor (20), and further has a position sensor for detecting a working position of the container (30, 32, 34).

12 Claims, 3 Drawing Sheets

SENSOR MODULE, TISSUE PROCESSOR, AND METHOD FOR OPERATING A TISSUE PROCESSOR

CROSS REFERENCE TO RELATED APPLICATIONS

This application claims priority of German patent application number 10 2010 017 667.2 filed Jun. 30, 2010, the entire disclosure of which is incorporated by reference herein.

FIELD OF THE INVENTION

The present invention relates to a sensor module for a tissue processor. The sensor module includes a thermal sensor for measuring a temperature of a container of the tissue processor. The present invention also relates to a tissue processor having a container for receiving a process medium, and further having the sensor module for measuring a temperature of the container. Moreover, the present invention relates to a method for operating the tissue processor.

BACKGROUND OF THE INVENTION

In order to examine samples, in particular tissue samples, using a microscope, the tissue samples frequently need to be prepared for this purpose. In particular, the samples need to be cut into extremely thin sections so that they can be examined with the microscope. Sectioning of the tissue samples is commonly done using microtomes. To enable accurate sectioning of the tissue samples, the samples are initially subjected to a treatment process. For example, they may be embedded in paraffin blocks. The embedding of the samples can be done using generally known tissue processors, which include a plurality of containers containing process media. In order to carry out the treatment, the samples are either placed in the containers, or in a retort which is provided for sample treatment and into which the process media are pumped from the containers.

When using process media, it is generally required to maintain the process parameters within predetermined limits. For example, when paraffin is used as a process medium, the paraffin is maintained at a predetermined desired temperature with an accuracy of ±2K, firstly to keep the paraffin in the liquid state, and secondly to prevent the additives contained in the paraffin from being damaged by overheating. In order to measure the temperature of the process media, it is known to provide a temperature sensor which measures the temperature of a container containing one or more process media. The process media temperature can be controlled to a predetermined desired value, or to different predetermined desired values, using a heating device.

During operation of the tissue processor, the containers are in their working position, in which the process medium is pumped out of or into the container. If during operation of the tissue processor, one of the containers is not in its predetermined working position, either because it was not placed in the tissue processor at all, or because it has not been completely brought into its working position, process medium may leak from the connections, conduits and/or from the tissue processor, contaminating the tissue processor or the environment surrounding it and/or impairing the proper functioning of the tissue processor. In addition, leaking hot or harmful process media can cause injury to operating personnel.

SUMMARY OF THE INVENTION

It is an object of the present invention to provide a sensor module, a tissue processor having the sensor module, and a method for operating the tissue processor, which, in a simple manner, will help ensure safe and reliable operation of the tissue processor.

This object is achieved by the features of the disclosed invention. Advantageous embodiments are set forth in the present specification.

According to a first aspect of the present invention, the sensor module includes a thermal sensor for measuring a temperature of a container of the tissue processor and a position sensor for detecting a working position of the container.

The sensor module has a modular design, which in this context means that the thermal sensor and the position sensor are structurally and functionally integrated with each other to form a single unit which can be fitted into and/or removed form the tissue processor as a whole. The modular design of the sensor module, and especially the integration of the thermal sensor and the position sensor into one unit, contributes in a particularly simple way to ensuring reliable operation of the tissue processor by making it possible both to measure the temperature of the container and to check whether the container is in its working position, using a single sensor module.

In an advantageous embodiment, the position sensor includes a first switch element which, in its first operating position, indicates that the container is in the working position. In its second operating position, the first switch element indicates that the container is not in the working position. The first switch element includes the thermal sensor. In other words, the thermal sensor forms part of a switch element of the position sensor, which emphasizes the modular design of the sensor module, and in particular the interaction between the thermal sensor and the position sensor. Integrating the thermal sensor into the first switch element enables a particularly compact design for the sensor module.

In another advantageous embodiment, the first switch element has a contact member for contacting the container. The contact member is spherical in shape and rotatably held in a corresponding bearing. In particular, the thermal sensor may be disposed in the spherical contact member. The spherical shape of the contact member helps ensure reliable operation of the first switching element, even if a wall of the container to be contacted by the first switch element is oblique relative to the contact member, which may be due to manufacturing tolerances.

A second aspect of the present invention relates to the tissue processor, which has a first container for receiving a first process medium, and a first sensor module. Preferably, the first sensor module is similar in design to the sensor module described hereinbefore. When using the first process medium, the first container is in its working position. The sensor module is disposed such that it detects whether the first container is in its working position and that it measures the temperature of the first container if the first container is in the working position. In other words, placing the first container into its working position will operate the position sensor of the sensor module.

When the first switch element of the sensor module is actuated by a wall of the container, it is also possible to measure the temperature of the wall, and thus of the process medium in the container, since the first switch element of the position sensor includes the contact member containing the thermal sensor, and because actuation of the first switch element by the wall of the container causes the thermal sensor to be thermally coupled to the wall of the container via the contact head.

In this connection, it is particularly advantageous that when the first container is in the working position, the first container presses against the first switch element containing the thermal sensor, and the first switch element is in its first operating position. If the first container is not in its working position, the first container does not press against the first switch element containing the thermal sensor in such a way that it is in its first operating position. Instead, the first switch element is then out of its first operating position and located in its second operating position. The first operating position includes any position in which the position sensor detects the first container to be in the working position. The second operating position includes any position in which the position sensor does not detect the presence of first container.

In a further advantageous embodiment, two ore more containers containing the same, similar or different process media are disposed in the tissue processor. Each of the containers is associated with a separate sensor module, which detects whether the respective container is in the working position, and which measures the temperature of the container and, in particular, of the process medium contained therein.

According to a third aspect of the present invention, the container is placed in a station of the tissue processor. It is then checked whether the container is located in its working position within the station, and its temperature is measured at the same time.

BRIEF DESCRIPTION OF THE DRAWING VIEWS

Exemplary embodiments of the present invention are described in more detail below with reference to the schematic drawings, in which.

DETAILED DESCRIPTION OF THE INVENTION

Figure 1:
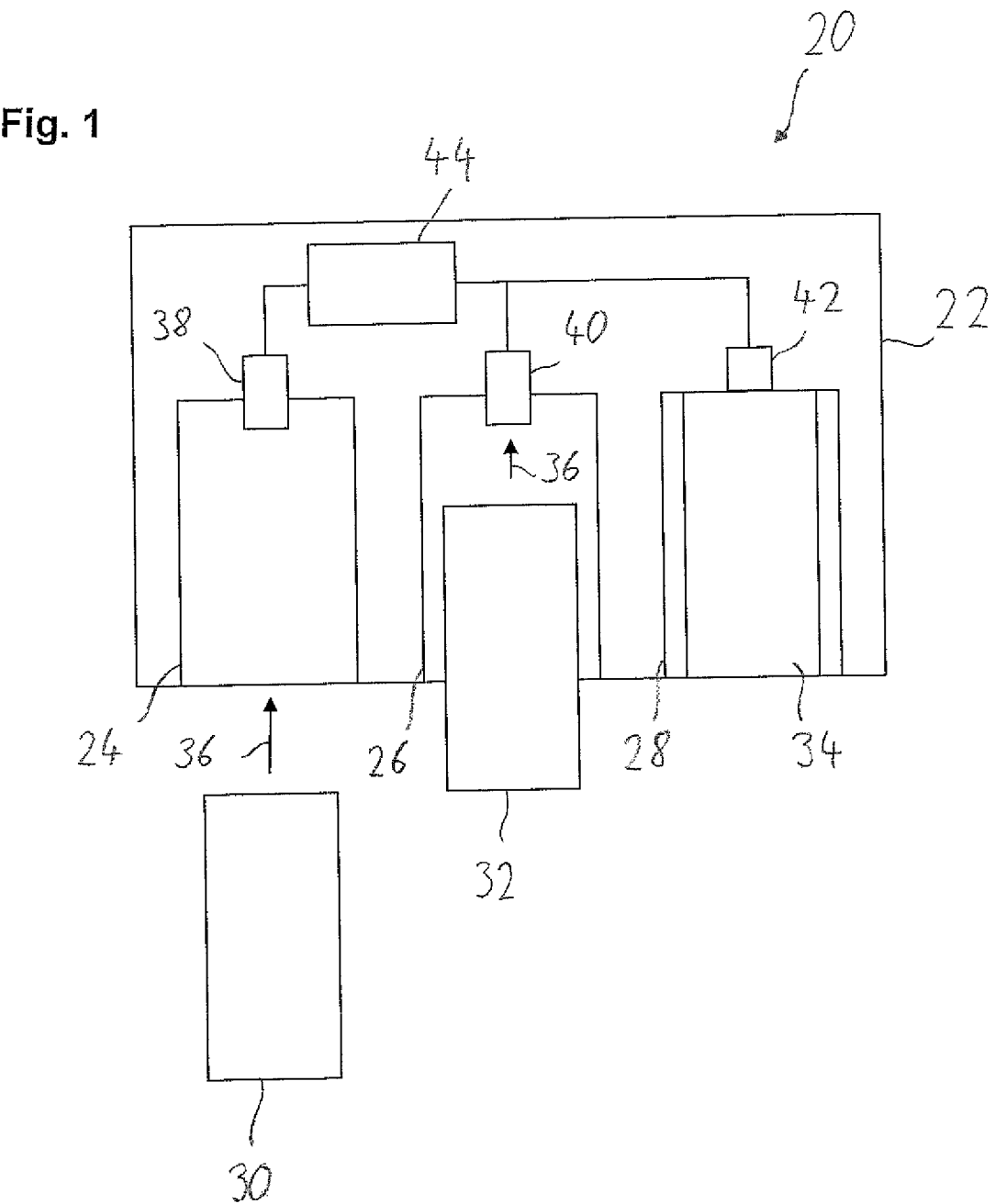
FIG. 1 is a view of a tissue processor.

Elements having the same design or function are identified by the same reference numerals throughout the figures.

FIG. 1 shows a tissue processor 20, which can be used to prepare samples, in particular tissue samples, in such a way that they can subsequently be cut with a microtome into fine slices, which may then be examined using a microscope. During processing in tissue processor 20, the tissue samples are successively exposed to different process media. For example, the samples are cleaned, dehydrated and embedded using alcohol, xylene, paraffin, and other process media, respectively.

Tissue processor 20 has a first station 24, a second station 26, and a third station 28 for receiving the process media. A first container 30 is insertable into first station 24 along an insertion direction 36. A second container 32 is partially inserted in second station 26, and may be inserted further along insertion direction 36. A third container 34 is completely inserted in third station 28. Third container 34 is in its working position. In contrast, first and second containers 30, 32 are out of their working position. In the working position, the process media may be pumped out of or into containers 30, 32, 34.

First processing station 24 is associated with a first sensor module 38. Second processing station 26 is associated with a second sensor module 40. Third processing station 28 is associated with a third sensor module 42. Sensor modules 38, 40, 42 are used to detect whether any of containers 30, 32, 34 is in its working position, and to measure the temperature of the respective container 30, 32, 34 and of the process medium contained therein. In order to measure the temperature of the process medium, the temperature of the respective container 30, 32, 34 is measured with the aid of sensor modules 38, 40, 42 and, as a function thereof, the temperature of the process medium in the respective container 30, 32, 34 is determined using, for example, an empirically established assignment rule. In the working position, sensor module 38, 40, 42 is preferably coupled to a rear wall of the respective container 30, 32, 34. During operation of tissue processor 20, the process media temperature is typically between 50° C. and 65° C., depending on the type of process medium. However, depending on the process medium, the temperature may be significantly higher or lower, particularly when using different kinds of paraffin and/or paraffin of different manufacturers.

In FIG. 1, third container 34 is in its working position. In the working position, third container 34 actuates third sensor module 42, as a result of which the third sensor module detects that third container 34 is in its working position. Moreover, there is direct contact between third sensor module 42 and a wall of third container 34, which allows easy and accurate measurement of the temperature of third container 34, and thus of the process medium contained therein.

Providing one sensor module 38, 40, 42 for each of containers 30, 32, 34 contributes to making it possible to measure the temperature of each of containers 30, 32, 34 individually with high accuracy and independently of the other containers 30, 32, 34. Sensor modules 38, 40, 42 are electrically coupled to a processing unit 44, which controls a heating device (not shown) adapted to heat containers 30, 32, 34 as a function of the output signals of sensor modules 38, 40, 42. Preferably, each of containers 30, 32, 34 can be heated individually by means of the heating device not shown. Thus, using sensor modules 38, 40, 42 and processing unit 44, the temperatures of the process media in containers 30, 32, 34 can be controlled independently of each other.

Figure 2:
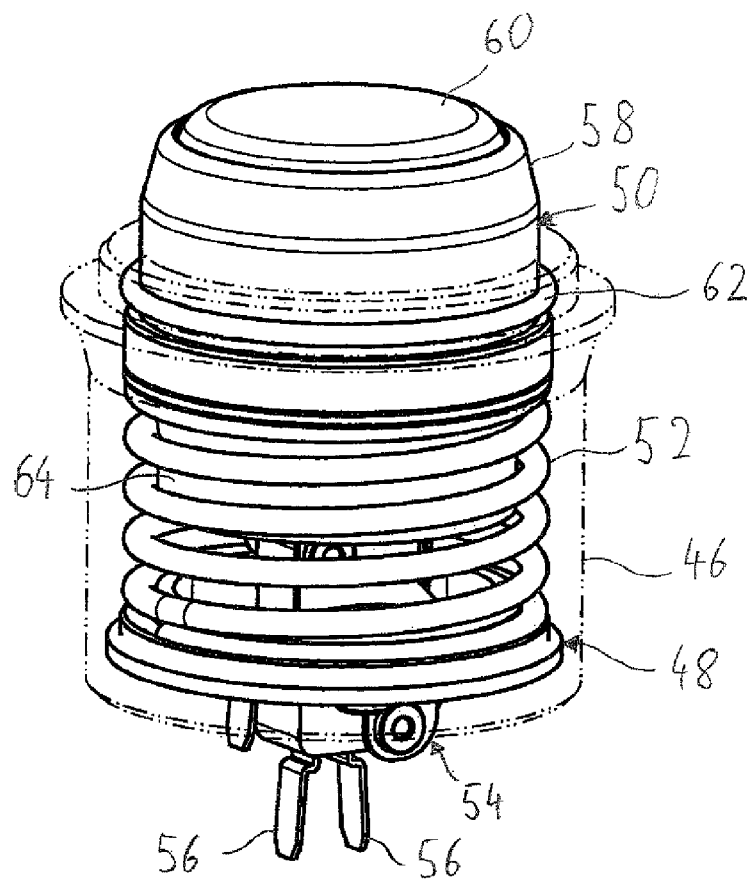
FIG. 2 is a perspective view of a sensor module.

FIG. 2 shows one of sensor modules 38, 40, 42 in a perspective view. Sensor module 38, 40, 42 includes a module housing 46, shown in FIG. 2 in double-dot-dash lines. Module housing 46 accommodates a first switch element 50 and a second switch element 48. During normal use in tissue processor 20, second switch element 48 is stationary and fixedly connected to tissue processor 20. First switch element 50 is mounted movably relative to second switch element 48. To this end, first switch element 50 is resiliently coupled to second switch element 48 by a resilient element 52, in particular a coil spring. The coil spring allows movement of first switch element 50 relative to second switch element 48, and more specifically in an axial direction of resilient element 52.

First switch element 50 includes a ball head 60 and a socket 58 for retaining and supporting ball head 60. Ball head 60 is partially spherical in shape and is rotatably supported with its spherical portion in the correspondingly configured socket 58. Apart from that, ball head 60 has a flattened region on its side facing away from second switch element 48, said flattened region being adapted to bear against a flat wall, in particular a rear wall, of containers 30, 32, 34 when containers 30, 32, 34 are in the working position, thereby creating a good thermal bridge between sensor module 38, 40, 42 and the respective container 30, 32, 34. Socket 58 is sealed from an environment surrounding sensor module 38, 40, 42 by means of an outer seal 62. First switch element 50 is closed by a closure member 64 in a direction toward second switch element 48.

Second switch element 48 includes a switch 54. Switch 54 has terminals 56 via which sensor module 38, 40, 42, in particular switch 54, can be coupled to processing unit 44.

Figure 3:
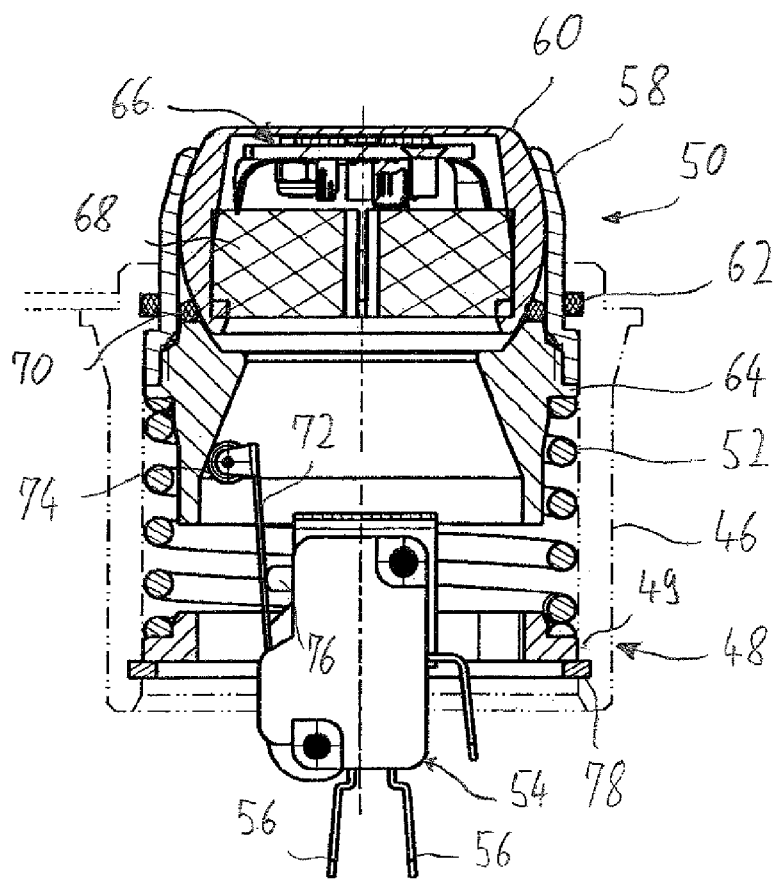
FIG. 3 is a transverse sectional view through the sensor module of FIG. 2.

FIG. 3 shows a section through sensor module 38, 40, 42 of FIG. 2. Ball head 60 has an inner cavity, which accommodates a thermal sensor 66 and an insulation 68, in particular a thermal insulation 68. Thermal sensor 66 is coupled directly to one side of ball head 60. This is the side at which ball head 60 is in contact with a wall of one of containers 30, 32, 34 when the respective container is in the working position. This allows the temperature of container 30, 32, 34 to be measured by thermal sensor 66 with high accuracy. Ball head 60 is disposed in socket 58 such that it can rotate in any plane, at least through small angles of between 1° and 15°. An inner seal 70 is disposed between socket 58, ball head 60, and closure member 64. The temperature of the process medium stored in a container 30, 32, 34 can be determined as a function of the temperature of the container.

Switch 54 takes the form of a roller lever switch including a switch-operating arm 72, a switch-operating roller 74, and a switch-operating button 76. Switch-operating roller 74 engages the inner surface of closure member 64 and is mounted on an axial end of switch-operating arm 72. Switch-operating arm 72 is pivotably secured to a housing of switch 54 opposite switch-operating roller 74. Alternatively or additionally, switch-operating arm 72 may be formed of a flexible material. Switch-operating button 76 is disposed between the housing of switch 54 and switch-operating arm 72. In the event of relative movement between first switch element 50 and second switch element 48, in particular when first switch element 50 moves in an axial direction toward second switch element 48, switch-operating roller 74 rolls along the inner surface of closure member 64. As a result, switch-operating arm 72 is pivoted and/or flexed, thereby urging switch-operating button 76 into its first operating position. The first operating position of switch-operating button 76 indicates that the respective container 30, 32, 34 is in its working position.

During insertion of containers 30, 32, 34 into the respective stations 24, 26, 28, initial contact with the respective sensor module 38, 40, 42 first causes the respective ball head 60 to align so that the side of ball head 60 facing the respective container 30, 32, 34 rests flat against the rear container wall. Further insertion of the respective container 30, 32, 34 then causes first switch element 50 to move toward second switch element 48, and more specifically into its first operating position, which indicates that the respective container 30, 32, 34 is in its working position. In the first operating position, first switch element 50, in particular closure member 64 of first switch element 50, acts upon second switch element 48, in particular upon switch-operating arm 72 of switch 54, in such a way that second switch element 48, in particular switch-operating arm 72 and switch-operating button 76, are each in their first operating position, whereby an output signal is generated which indicates that the respective container 30, 32, 34 is in its working position. If container 30, 32, 34 is not in its working position, the first switch element of the respective sensor module 38, 40, 42 is out of its first operating position, and more specifically in its second operating position, in which switch-operating arm 72 a switch-operating button 76 are also out of their first operating position, and more specifically in their second operating position, in which no output signal is generated which would indicate that the respective container 30, 32, 34 is in its working position.

Figure 4:
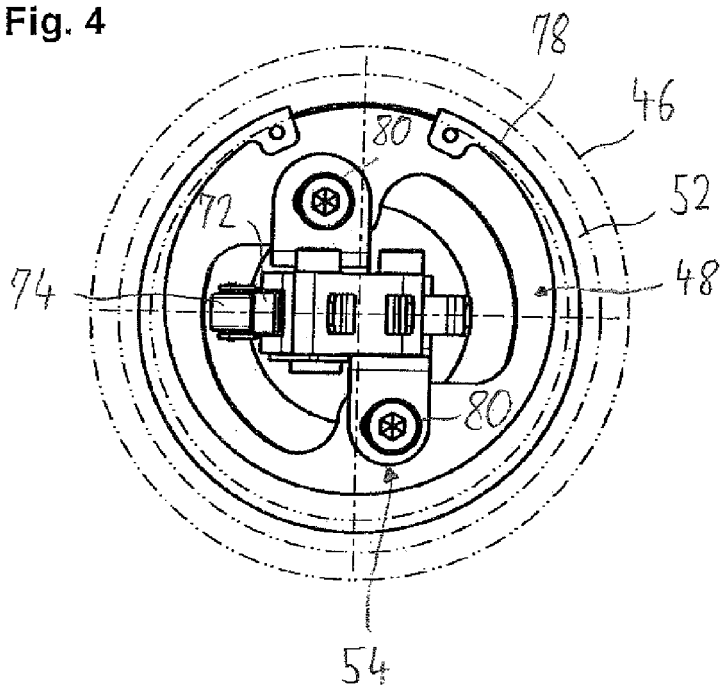
FIG. 4 is a longitudinal sectional view through the sensor module of FIG. 2.

FIG. 4 shows a longitudinal section through sensor module 38, 40, 42 of FIG. 2. The longitudinal section shows second switch element 48 in a view from above. Switch 54 is secured to a base plate 49 of second switch element 48. The second switch element is secured in module housing 46 by a clamping ring 78.

Figure 5:
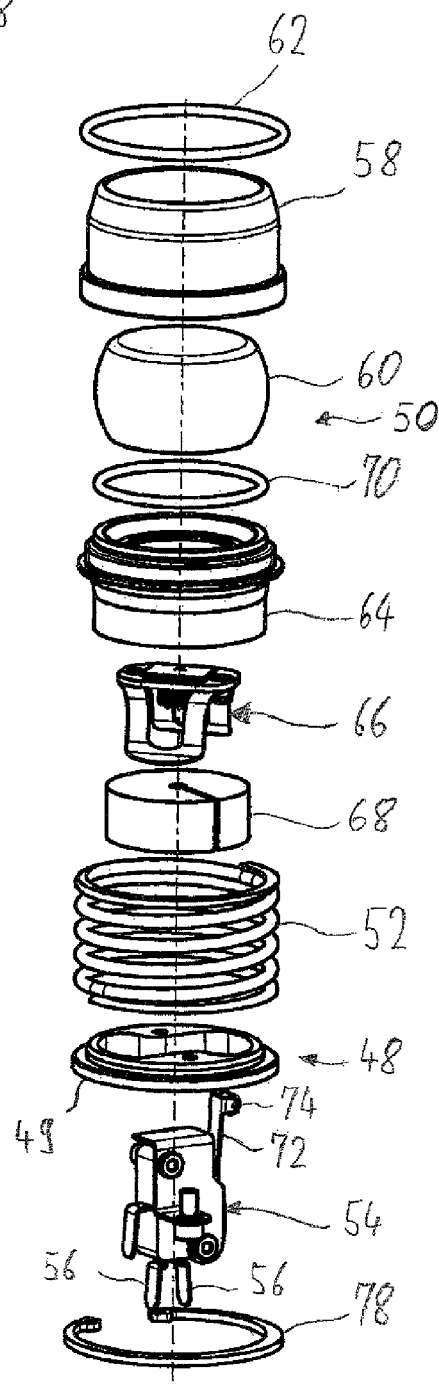
FIG. 5 is an exploded view of the sensor module of FIG. 2.

FIG. 5 shows an exploded view of sensor module 38, 40, 42. In order to assemble sensor 38, 40, 42, it is preferred to initially assemble first switch element 50. In particular, thermal sensor 66 and insulation 68 are inserted into ball head 60. Then, ball head 60 is inserted into socket 58 along with inner seal 70, and is closed by closure member 64. To this end, closure member 64 may, for example, be screwed into socket 58 via a thread. Subsequently, second switch element 48 is assembled, for example by fixing switch 54 with fastening means 80 to base plate 49 of second switch element 48. Resilient element 52 is placed over second switch element 48, and then first switch element 50 is placed onto elastic element 52. The assembly put together in this way is secured in module housing 46 by clamping ring 78. The so-configured sensor module 38, 40, 42 constitutes a complete unit, and can be easily fitted into and removed from the tissue processor. This facilitates maintenance of tissue processor 20. Moreover, since sensor module 38, 40, 42 is a completely closed modular unit, thermal sensor 66 and the position sensor are protected from being contaminated by, for example, one of the process media. Furthermore, the individual stations 24, 26, 28 can be easily cleaned without damaging or contaminating sensor modules 38, 40, 42.

The modular design of sensor modules 38, 40, 42 contributes in a particularly simple way to allowing reliable operation of tissue processor 20. In particular, it is possible, in a particularly simple way, to measure the temperature of the process media in the individual containers 30, 32, 34 with high accuracy and, at the same time, to check whether the respective containers 30, 32, 34 are in their working position. The compact nature of the design is emphasized by the synergetic effect of the two sensor units, in particular by the fact that thermal sensor 66 is integrated into the moving elements that serve to actuate the position sensor.

The present invention is not limited to the exemplary embodiments described herein. For example, second switch element 48 may be of any design that allows the position sensor to be actuated by the movement of thermal sensor 66. Further, as an alternative to incorporating thermal sensor 66 in ball head 60, it may also be mounted in a normal, for example cylindrical pressure head. Moreover, resilient element 52 may be one other than the spring. In addition, as an alternative to the roller lever switch, any other suitable switch may be used as switch 54.

LIST OF REFERENCE NUMERALS 20 tissue processor
22 processor housing
24 first station
26 second station
28 third station
30 first container
32 second container
34 third container
36 insertion direction
38 first sensor module
40 second sensor module
42 third sensor module
44 processing unit
46 module housing
48 second switch element
49 base plate
50 first switch element 52 resilient element
54 switch
56 terminals
58 socket
60 ball head
62 outer seal
64 closure member
66 thermal sensor
68 insulation
70 inner seal
72 switch-operating arm
74 switch-operating roller
76 switch-operating button
78 clamping ring
80 fastening means

What is claimed is:

1. A sensor module for a tissue processor, the sensor module comprising:
a thermal sensor for measuring a temperature of a container of the tissue processor; and
a position sensor for detecting a working position of the container;
wherein the position sensor includes a first switch element having a first operating position in which the first switch element indicates that the container is in the working position and a second operating position in which the first switch element indicates that the container is not in the working position, and wherein the first switch element includes the thermal sensor;
wherein the thermal sensor is configured to displace relative to the position sensor when the first switch element is moved between the first operating position and the second operating position.

2. The sensor module as recited in claim 1, wherein the position sensor further includes a second switch element responsive to movement of the first switch element into the first operating position thereof such that the sensor module generates an output signal indicating that the container is in the working position.

3. The sensor module as recited in claim 1, wherein a portion of the second switch element is stationary.

4. The sensor module as recited in claim 2, wherein the second switch element includes a switch-operating button and a pivotably mounted switch-operating arm; the switch-operating arm being coupled with the switch-operating button and having a rotatable roller which is coupled with the first switch element; the switch-operating arm, the roller and the first switch element being configured and arranged relative to each other in such a way that a movement of the first switch element relative to the second switch element causes the roller to roll along a surface of the first switch element to thereby cause the switch-operating arm to pivot such that the switch-operating arm actuates the switch-operating button.

5. The sensor module as recited in claim 2, further comprising a resilient element between the first and second switch elements for biasing the first switch element in a direction toward the second operating position.

6. The sensor module as recited in claim 1, wherein the first switch element has a contact member for contacting the container, the contact member being spherical in shape and rotatably held in a corresponding bearing.

7. The sensor module as recited in claim 6, wherein the thermal sensor is coupled with the spherical contact member.

8. The sensor module as recited in claim 7, wherein the thermal sensor is disposed in the spherical contact member.

9. A tissue processor for processing tissue samples, the tissue processor comprising:
at least one container locatable in a respective working position and adapted to receive a respective process medium when located in the respective working position; and
at least one sensor module, each sensor module including a thermal sensor and a position sensor;
wherein each container has a corresponding respective sensor module disposed to detect whether such container is in its respective working position, with a position sensor, and to measure the temperature of such container, with a temperature sensor, when such container is in its respective working position;
wherein the corresponding respective sensor module includes a first switch element having a first operating position in which the first switch element indicates that the respective container is in the working position and a second operating position in which the first switch element indicates that the respective container is not in the working position, and wherein the first switch element includes the thermal sensor;
wherein the thermal sensor is configured to displace relative to the position sensor when the first switch element is moved between the first operating position and the second operating position.

10. The tissue processor as recited in claim 9, wherein the position sensor includes a first switch element having a first operating position in which the first switch element indicates that the corresponding container is in its respective working position and a second operating position in which the first switch element indicates that the corresponding container is not in its respective working position, and the first switch element carries the thermal sensor, and wherein each sensor module is arranged such that when the corresponding container is in its respective working position, the corresponding container presses against the first switch element carrying the thermal sensor and the first switch element is moved to the first operating position; and when the corresponding container is not in its respective working position, the corresponding container does not press against the first switch element carrying the thermal sensor, and the first switch element is in the second operating position.

11. The tissue processor as recited in claim 9, wherein the at least one container comprises a plurality of containers for receiving a plurality of process media, and the at least one sensor module comprises a plurality of sensor modules associated one sensor module with each of the plurality of containers.

12. A method for operating a tissue processor comprising the steps of:
inserting a container for receiving a process medium into a station of the tissue processor;
determining whether the container in the station is in a working position with a position sensor; and
measuring a temperature of the container with a thermal sensor at the same time the container is determined to be in the working position;
wherein the position sensor includes a first switch element having a first operating position in which the first switch element indicates that the container is in the working position and a second operating position in which the first switch element indicates that the container is not in the working position, and wherein the first switch element includes the thermal sensor;
wherein the thermal sensor is configured to displace relative to the position sensor when the first switch element is moved between the first operating position and the second operating position.

* * * * *